United States Patent [19]

Lee et al.

[11] 3,933,882

[45] Jan. 20, 1976

[54] TUBE METHOD FOR THE PREPARATION OF OLEFINIC SILOXANE COMPOUNDS

[75] Inventors: Chi-Long Lee; Myron T. Maxson, both of Midland, Mich.

[73] Assignee: Dow Corning Corporation, Midland, Mich.

[22] Filed: Dec. 2, 1974

[21] Appl. No.: 528,960

[52] U.S. Cl. .................. 260/448.2 E; 260/46.5 R; 260/46.5 UA; 260/448.8 R; 252/429 R; 252/431 R
[51] Int. Cl.² ..... C07F 7/02; C07F 7/08; C07F 7/18
[58] Field of Search ........... 260/448.2 E, 448.8 R, 46.5 R, 260/46.5 UA; 252/429 R, 431 R

[56] References Cited
UNITED STATES PATENTS

| | | | |
|---|---|---|---|
| 2,823,218 | 2/1958 | Speier et al. | 260/448.2 E |
| 3,404,169 | 10/1968 | Gaignon et al. | 260/448.2 E |
| 3,419,593 | 12/1968 | Willing | 260/448.2 E |
| 3,453,233 | 7/1969 | Flatt | 260/46.5 UA |
| 3,576,027 | 4/1971 | Fish | 260/448.2 E |
| 3,775,452 | 11/1973 | Karstedt | 260/448.2 E X |
| 3,814,730 | 6/1974 | Karstedt | 260/46.5 UA |

*Primary Examiner*—Paul F. Shaver
*Attorney, Agent, or Firm*—Roger H. Borrousch

[57] ABSTRACT

A vaporized mixture of a platinum catalyst in the amount of 0.01 to 2 p.p.m. platinum, an acetylenic alcohol and a siloxane compound having at least three silicon-bonded hydrogen atoms per molecule is passed through a tube such as a stainless steel tube heated at 210°C. to 450°C. to produce an olefinic siloxane compound which is, below 100°C., an inhibitor for the reaction between the acetylenic alcohol and the siloxane compound having at least three silicon-bonded hydrogen atoms in the presence of platinum.

14 Claims, No Drawings

TUBE METHOD FOR THE PREPARATION OF OLEFINIC SILOXANE COMPOUNDS

BACKGROUND OF THE INVENTION

1. Field of the Invention

This invention relates to a method of preparing a siloxane compound having olefinic unsaturation.

2. Description of the Prior Art

The reaction between compounds having aliphatically unsaturated carbon linkages such as C=C or C≡C with silicon compounds having silicon-bonded hydrogen atoms in the presence of platinum to form new silicon compounds is well known in the art and is known as hydrosilation. A patent by John L. Speier and Donald E. Hook, U.S. Pat. No. 2,823,218, teaches that such reactions can be carried out in the presence of chloroplatinic acid. Speier et al. teach that both olefinic compounds and acetylenic compounds readily react to form new silicon compounds wherein the SiH adds across the unsaturated carbon bonds with a high product yield. Speier et al. also teach that the presence of other substituents in the unsaturated molecule, whether they be functional or entirely inert, does not prohibit the reaction. The unsaturated compounds which undergo reaction are taught as including unsaturated alcohols such as allyl alcohol, methylvinylcarbinol and ethynyldimethylcarbinol. Speier et al. teach that if an unsaturated alcohol is employed, a competing alcoholysis reaction will take place, but the reactants will no longer be those introduced where the source for the SiH is a silane, however, in general this problem does not arise when a siloxane is used as the source of SiH because the siloxanes are relatively inert to any extraneous substituents in the unsaturated reactant.

Speier et al. teach that the reaction temperature can vary over an extremely wide temperature range and optimum temperatures depend upon the concentration of catalyst present and the nature of the reactants. Temperatures suggested range from 0°C. to below 300°C. The temperature should be such that at least one of the reactants or a portion of the reaction mixture is in a mobile stage, liquid or gaseous and the maximum temperature is determined only by the stability of the reactants and the operator's desire to avoid decomposition products.

Speier et al. teach that the reaction time is variable and depends upon the reactants, reaction temperature and catalyst concentration among other things. Contact times of greater than 16 or 17 hours do no harm unless an extremely elevated temperature is employed, however, many reactants give a practically quantitative yield with contact times of 30 minutes or less and often an excellent yield can be obtained as soon as the exothermic reaction has begun which may be a matter of seconds. Speier et al. also teach that the reaction can be carried out at atmospheric, subatmospheric or superatmospheric pressures. The choice of conditions is a matter of logic based upon the nature of the reactants and the equipment available where nonvolatile reactants are adaptable to being heated at atmospheric pressure with or without reflux and gaseous reactants at ordinary temperatures are preferably reacted at substantially constant volume under autogenous or induced pressure wherein the best results are obtained by maintaining at least a portion of the reactants in the liquid phase.

Speier et al., as well as others, have been concerned with obtaining addition products from the reaction of aliphatically unsaturated compounds and silicon compounds having silicon-bonded-hydrogen atoms. However, none have suggested that there are situations where the product of such a reaction is an inhibitor for the very reaction by which it is made. Thus, the reaction begins but as soon as a small amount of product is produced the reaction stops because the products inhibit the reaction by poisoning the catalyst.

The present invention is directed to a preparation of a unique class of compounds which inhibit the catalyst at low temperatures but not at high temperatures. Because the catalyst which is inhibited is used to make the inhibiting compound, the preparation method to provide a commercially suitable process was not obvious. The inhibiting compounds are a class of siloxane compounds containing olefinic unsaturation and are prepared from acetylenic alcohols and siloxane compounds having silicon-bonded-hydrogen atoms. The earliest work did not produce an inhibiting compound for the platinum catalyzed addition of aliphatic unsaturation to silicon-bonded hydrogen, but instead provided a complex mixture which may be called "a crosslinker-catalyst-inhibitor." This work is the subject of a copending application Ser. No. 528,962, filed Dec. 2, 1974, entitled "Crosslinker-Platinum Catalyst-Inhibitor and Method of Preparation Thereof" by Randolph G. Niemi filed on even date herewith and assigned to the same party.

Niemi combined polysiloxane having multiple silicon-bonded hydrogen atoms, a platinum catalyst and an acetylenic alcohol, heated the mixture for about 16 hours at 70°C. and obtained a complex mixture after removing unreacted acetylenic alcohol by reduced pressure at room temperature, which when mixed with vinyl containing siloxane polymers remained uncured at room temperature but would cure at elevated temperatures. Thus, Niemi had found one could make room temperatue stable compositions from his mixture, but for each composition a separate mixture of crosslinker, catalyst and acetylenic alcohol was required. Attempts to separate the complex mixture into various components were impractical and expensive. The product could not be characterized to identify any particular species which were responsible for the inhibiting effects on platinum catalysts.

Using the method of Niemi, Chi-Long Lee and Ollie W. Marko as described in a copending application Ser. No. 528,966, filed Dec. 2, 1974, entitled "Olefinic Siloxanes As Platinum Inhibitors" filed on even date herewith and assigned to the same party prepared specific olefinic siloxane compounds which were inhibitors for the platinum catalysts in the addition reaction between aliphatic unsaturation and silicon-bonded hydrogen atoms. For example, Lee and Marko mixed equal molar quantities of (I) 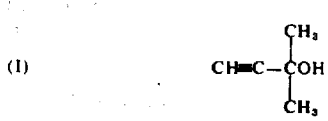

and (II) 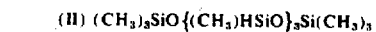

with a catalytic amount of a platinum catalyst from 2 to 50 parts per million platinum, heated the mixture at 70°C. for 16 hours, stripped off the unreacted starting ingredients, left set over night and then vacuum distillation was used to recover the product. The product was an olefinic siloxane compound of the formula

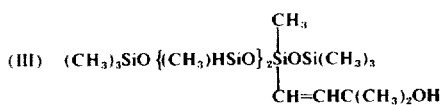

(III)  (CH$_3$)$_3$SiO {(CH$_3$)HSiO}$_2$SiOSi(CH$_3$)$_3$
          |
          CH=CHC(CH$_3$)$_2$OH

This compound mixed with a vinylsiloxane polymer, a silicon-bonded hydrogen containing compound and a platinum catalyst did not cure at room temperature in 10 days but when heated to 150°C. the composition cured in 2 minutes. Thus, this compound is a platinum catalyst inhibitor at room temperature, but not at elevated temperature.

Although Lee and Marko were able to characterize specific inhibitor compounds, the method of preparation was impractical. The process provided only a low conversion from 2 to 20 percent and the yield was less than 5 percent after distillation. In addition to both low conversion and yield, the reaction was difficult to control and could become violently exothermic, thus creating a safety hazard.

To improve the process, Lee and Marko discovered that the inhibitor could be prepared in a gas liquid chromatographic column as described in a copending application Ser. No. 528,959, filed Dec. 2, 1974, entitled "Method of Preparing Olefinic Siloxane By GLC" filed on even date herewith and assigned to the same party. Lee and Marko coated the injection port of a GLC column with a layer of platinum catalyst, heated the port at 350°C. and injected a mixture of (I) and (II) while maintaining the column at 300° to 400°C. The product (III) was obtained in yields of from 30 to 35 percent. This process had advantage over the Niemi process in that less platinum catalyst was used, very short residence times down to 1 to 2 seconds were needed, the yields were higher, high purity product was obtained and separate distillations were not needed. However, the method was not suitable for the production of large amounts of olefinic siloxane inhibitor. When larger GLC columns were used the yields decreased and the column became plugged by gelled materials. Thus, for small scale operations this method was found suitable but was deficient for large scale production.

SUMMARY OF THE INVENTION

This invention relates to a method for preparing olefinic siloxane compounds by passing a vaporized mixture of a platinum catalyst, an acetylenic alcohol and a siloxane compound having at least three silicon-bonded hydrogen atoms through a heated tube. The olefinic siloxane compound which contains at least one silicon-bonded hydrogen atom is an inhibitor at room temperature for the reaction between aliphatically unsaturated compounds and silicon-bonded hydrogen atoms in the presence of a platinum catalyst but allows the reaction to occur at elevated temperatures.

DESCRIPTION OF THE INVENTION

This invention relates to a method of reacting an acetylenic alcohol with a siloxane compound having at least three silicon-bonded hydrogen atoms bonded to at least three different silicon atoms in the presence of a platinum catalyst to provide an olefinic siloxane compound wherein the olefinic siloxane compound is an inhibitor for the platinum catalyst comprising passing a vaporized mixture of acetylenic alcohol, a soluble platinum catalyst and the siloxane compound having at least three silicon-bonded hydrogen atoms through a tube heated at a temperature of from 210°C. to 450°C. and collecting a reaction product which is an olefinic siloxane compound which is, below 100°C., an inhibitor for the reaction between the acetylenic alcohol and the siloxane compound having at least three silicon-bonded-hydrogen atoms in the presence of a platinum catalyst, said mixture containing from 0.01 to 2 parts by weight platinum per one million parts by weight mixture.

The method of this invention requires a feed means, a tube which can be heated and a collection means. The feed means can be any device which could be used to introduce a liquid mixture into a chamber, the tube, wherein the chamber contains vapors of the mixture. Thus, the feed may be gravity feed, injection feed (forced feed) and the like wherein the appropriate valves or other means are used to prevent the vapors of the heated chamber from reversing. The feed means may be automated to give a constant feed or spaced interval feeding of the feed may be done manually or by gravity depending upon the sophistication desired.

The tube or chamber can be of any reasonable shape as long as the vapors can pass through. The tube can be a straight tube, a coiled tube, an S shaped tube and the like. The tube can be made of any material which will withstand the temperatures of this method and which is inert to the reactants and products, such as stainless steel or glass. The tube is heated by any conventional means which allows control of the temperature such as an oven, a bath and the like.

The tube can be any reasonable length to provide for the reaction mixture a residence time of from 5 to 120 seconds in the heated tube. Thus, the flow rate and tube length combined with tube diameter can be varied over a broad range of enumerable combinations to provide in the heated zone a residence time within the range defined.

The collection means is a cooled area which allows the vapors to condense. The condensed vapors will be the reaction product and can be condensed by a single condenser or by a multiple condenser system in series. The single condenser collects all the reaction product and further distillation of the reaction product is required to obtain the desirable olefinic siloxane inhibitors which are adducts of the acetylenic alcohol and the siloxane compound having at least three silicon-bonded hydrogen atoms (SiH). This distillation can be carried out under reduced pressure and because there is little platinum present in the reaction product, the amount of undesirable polymerization and degradation is minimized. If a multiple condenser system is used, the high boiling materials of the reaction mixture can be removed first by passing the vapors through a condenser which is at a temperature higher than the olefinic siloxane compounds desired out below the temperature of the undesirable high boiling materials. The vapors of the reaction mixture minus these high boiling materials is then passed through a second condenser at a temperature below the boiling point of the olefinic siloxane compounds but above the boiling points of the unreacted starting materials. Thus, the olefinic siloxane compounds can be obtained without a distillation. The unreacted starting materials are then collected separately by passing the remaining vapors through additional condensers of appropriate temperature. Thus, if the reactants are 3-methyl-1-butyn-3-ol, boiling point of 105°C., the siloxane of formula (II), boiling point of 206°C. and the mono-adduct of formula (III), boiling point of 265°C., four condensers could be used. The reaction product vapors could be passed through a first condenser at a temperature of 270°C. where the high boiling materials are condensed and removed from the vapor mixture, a second condenser at 250°C. would condense the mono-adduct of formula (III) a third condenser at 180°C. would condense the siloxane of formula (II) from the vapors and a fourth condenser at 80°C. would condense the 3-methyl-1-butyn-3-ol. The unreacted starting materials could then be recycled for further reaction.

The present method avoids the hot spots which can develop in a GLC method as described in the application of Lee and Marko cited above and also reduces the tendency of the GLC column of separating the reaction ingredients before they have an opportunity to react and thus the yields are higher. However, this method is also prone to plugging on long continuous use. Still separation advantages can be realized wherein certain products are difficult to distill, especially using the multi-condenser system in collecting the products. Also this method can provide larger quantities of highly pure products than can be obtained from the GLC method in the same time period. The yield of olefinic siloxane compound which are inhibitors can be up to 60 percent using this method.

The mixture of reactants can be carried through the tube with an inert carrier gas such as helium, neon, argon and nitrogen. Reactive carrier gases such as hydrogen gas should not be used in this method.

The acetylenic alcohol can be any of those alcohols having a C≡C bond which when reacted with a siloxane compound having SiH results in an olefinic containing siloxane which are inhibitors for platinum catalyst at room temperature but not at elevated temperatures above 100°C. Examples of such acetylenic alcohols, include, 3-methyl-1-buytyn-3-ol, 1-ethynylcyclohexan-1-ol, 3,5-dimethyl-1-hexyn-3-ol, 3-methyl-1-pentyn-3-ol and the like.

The siloxane compounds are those having at least three silicon-bonded hydrogen atoms bonded to at least three separate silicon atoms. These siloxane compounds can be straight chains, cyclics, or branched. These siloxanes can be copolymers, homopolymers, single species, mixtures of the various types mentioned above. The only requirement of these siloxane compounds is that they be capable of being vaporized at the temperature used herein. It is preferred that these siloxane compounds have at least two silicon-bonded hydrogen atoms bonded to silicon atoms separated by one oxygen atom, preferably three silicon-bonded hydrogen atoms bonded to three silicon atoms which are only separated by oxygen. Some of the siloxane compounds for use in the present method are defined by the following generic formulae, R$_3$SiO(RHSiO)$_x$SiR$_3$, HR$_2$SiO(RHSiO)$_u$SiR$_2$H, (RHSiO)$_y$, HR$_2$SiO(RHSiO)$_u$(R$_2$SiO)$_z$SiR$_2$H, R$_3$SiO(R$_2$SiO)$_z$(RHSiO)$_x$SiR$_3$, HR$_2$SiO(RHSiO)$_v$SiR$_3$, HR$_2$SiO(R$_2$SiO)$_z$(RHSiO)$_v$SiR$_3$,

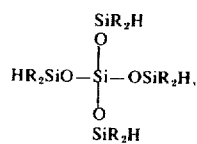

and the like, wherein each R is a monovalent hydrocarbon radical having no aliphatic unsaturation such as methyl, ethyl, phenyl, propyl, hexyl cyclohexyl, octyl, dodecyl, cyclopentyl, isopropyl, or fluorinated monovalent hydrocarbon radicals such as 3,3,3-trifluoropropyl, other perfluoroalkylethyl radicals, α, α, α-trifluoromethylphenyl, hexafluorophenyl and the like. The number of siloxane units per molecule can vary from as little as 3 to any number which can be passed through the system, preferably from 3 to 50 siloxane units per molecule. Other siloxane compounds are also suitable such as those which have arylene or alkylene bonds between some of the silicon atoms. Some specific siloxane compounds include

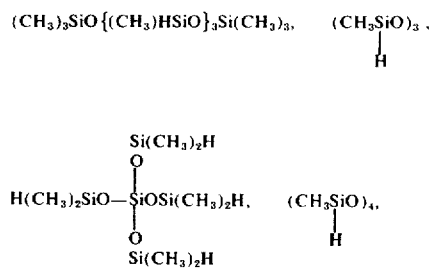

and the like.

The soluble platinum catalyst is not narrowly critical and can be chloroplatinic acid, platinum chlorides, platinum salts, platinous halide complexes with olefins and other well known platinum catalysts. These and other platinum catalyst are further defined and illustrated in U.S. Pat. No. 3,453,234, issued July 1, 1969 to Gust J. Kookootsedes, and hereby included by reference to illustrate platinum catalyst. By the term "soluble platinum catalyst" it is to be understood that it is soluble in the mixture to be vaporized.

The amount of acetylenic alcohol and siloxane compound having silicon-bonded hydrogen atoms can vary broadly. Molar ratios of one to one have been found suitable, however, the ratio of acetylenic alcohol to siloxane compound can be varied outside this ratio and still obtain a product but the yield will drop. Wherein ratios of less than 1/1 are used the amount of product obtained even at 100 percent conversion will be less than obtainable when a 1/1 ratio is used, however, the amount of mono-adduct is increased compared to di-adduct and multi-adduct.

The amount of platinum catalyst is critical for the upper limit because decomposition can become prominent if too much platinum is present. Amounts in the order of 0.01 parts by weight platinum per million parts by weight of acetylenic alcohol and siloxane compound are suitable. The maximum amount is determined by the amount which will cause the reaction to proceed without significant decomposition. This maximum amount will depend upon the type of siloxane compound, acetylenic alcohol and platinum catalyst, as well as the temperature of reaction. Generally, less platinum catalyst is required the higher the reaction temperature. For most reactions, amounts from 0.1 to 2 parts per million platinum can be used, but caution should be taken to prevent decomposition at the higher concentrations. Preferably, the amount of platinum does not exceed 1.0 p.p.m. platinum.

The method of this invention produces an olefinic siloxane compound which is the addition product of the acetylenic alcohol and the siloxane compound having at least three silicon-bonded hydrogen atoms. The addition products, which are produced in major amounts and which are the inhibitors, are those which do not add to all the silicon-bonded hydrogen atoms. There should be at least one unreacted silicon-bonded hydrogen bond per molecule of olefinic siloxane compound. The method of this invention provides addition products which are inhibitors in amounts of greater than 80 percent combined mono-adducts and di-adducts. Both the mono- and di-adducts are inhibitors, however, when all the silicon-bonded hydrogen atoms are reacted the product is markedly reduced in inhibition activity.

di-adduct, tri-adduct and unreacted siloxane (II) and then multiplied by 100. The percent yield was the area of the mono-adduct divided by the sum of the areas for the mono-adduct, di-adduct and tri-adduct. The siloxane compound used was the siloxane defined by formula (II) and the acetylenic alcohol was 3-methyl-1-butyn-3-ol. The platinum catalyst was a chloroplatinic acid complex with symmetrical divinyltetramethyldisiloxane having about 0.65 weight percent platinum and prepared as described in U.S. Pat. No. 3,419,593 which is hereby incorporated by reference. The feed mixture was a mixture of the siloxane, acetylenic alcohol and platinum catalyst. The tube diameter was measured as the outside diameter.

Table 1

| Ref. No. | Tube Diameter, cm. | Tube Length m. | Bath Temperature, °C. | Feed Rate, ml./hr. | Molar Ratio of Acetylenic Alcohol to Siloxane | Platinum Concentration, p.p.m. | % Conversion | % Yield |
|---|---|---|---|---|---|---|---|---|
| 1 | 0.635 | 1.524 | 350 | 15 | 1.0 | 0.10 | 8.42 | 96.00 |
| 2 | 0.9525 | 3.084 | 375 | 15 | 1.5 | 0.10 | 9.93 | 96.29 |
| 3 | 0.635 | 3.084 | 375 | 30 | 1.5 | 0.10 | 7.45 | 100 |
| 4 | 0.9525 | 1.524 | 375 | 30 | 1.5 | 0.10 | 3.88 | 100 |
| 5 | 0.9525 | 1.524 | 350 | 30 | 1.5 | 0.25 | 29.20 | 84.85 |
| 6 | 0.9525 | 1.524 | 375 | 30 | 1.0 | 0.25 | 43.69 | 84.44 |
| 7 | 0.9525 | 3.084 | 350 | 15 | 1.5 | 0.25 | 9.29 | 88.2 |
| 8 | 0.9525 | 3.084 | 375 | 15 | 1.0 | 0.25 | 23.0 | 97.96 |
| 9 | 0.635 | 3.084 | 350 | 30 | 1.0 | 0.10 | 10.04 | 95.65 |
| 10 | 0.9525 | 3.084 | 350 | 15 | 1.0 | 0.10 | 2.52 | 100 |
| 11 | 0.635 | 1.524 | 350 | 15 | 1.5 | 0.25 | 24.34 | 87.75 |
| 12 | 0.635 | 3.084 | 350 | 15 | 1.5 | 0.25 | 28.98 | 80.00 |
| 13 | 0.635 | 1.524 | 375 | 15 | 1.0 | 0.25 | 50.37 | 68.65 |
| 14 | 0.635 | 1.524 | 375 | 15 | 1.0 | 0.25 | 50.37 | 68.65 |
| 15 | 0.9525 | 1.524 | 350 | 30 | 1.0 | 0.10 | 4.90 | 92.30 |
| 16 | 0.635 | 3.084 | 375 | 30 | 1.0 | 0.25 | 42.85 | 84.32 |

The olefinic siloxane compound inhibitors are useful in that these compounds retard the room temperature reaction of vinyl compounds with silicon-bonded hydrogen atoms which are catalyzed with platinum but allow the reaction to occur rapidly at elevated temperature such as at 150°C. Thus, these olefinic siloxane compounds can be used to make one package compositions which cure on heating but are stable over extended periods of time at ambient conditions.

The following examples are presented for illustrative purposes and should not be construed as limiting the invention which is properly delineated in the appended claims.

EXAMPLE 1

Reactions to produce olefinic siloxane compounds were prepared under varying conditions using a helium gas carrier, a stainless steel tube, a salt bath surrounding the tube to control the heat, a water cooled condenser to collect the reaction product and a pump to regulate the feed rate of the mixture. The varying conditions were as defined in Table 1 wherein the percent conversions and percent yields were as shown. The percent conversion and percent yield were determined by integrating the areas under the peaks of a GLC chromatogram. The percent conversion was the sum of the areas for the mono-adduct, di-adduct, tri-adduct divided by the sum of the areas for the mono-adduct,

EXAMPLE 2

The method described in Example 1 was followed where the tube was 0.635 cm. in diameter and 1.219 meters long, 0.1 p.p.m. platinum was used, a helium flow of 11.8 cubic centimeters per minute was used, a 1.0 molar ratio of acetylenic alcohol to siloxane was used and a 0.1 milliliter sample of mixture was injected every 60 seconds into the tube over a 6 hour period where the tube was at 350°C. heated in an oven. The resulting product was collected and distilled under reduced pressure and was found to contain 26.7 weight percent mono-adduct of formula (III), 49.6 weight percent unreacted siloxane of formula (II), 9.9 weight percent of a residue and 13.8 weight percent of 3-methyl-1-butyn-3-ol and any other low boiling materials.

EXAMPLE 3

The procedure of Example 2 was used except the helium flow rate was 17.8 cubic centimeters per minute, and the platinum concentration, tube temperature and sample size injected were as defined in Table 2. The relative amount of mono-adduct was followed by using a GLC analysis where the peak height of the mono-adduct of formula (III) was divided by the peak height of the unreacted siloxane of formula (II). Table 2 indicates this as the product ratio. Also indicated in Table 2 is those runs where degradation was observed.

Table 2

| Ref. No. | Oven Temperature, °C. | Platinum Concentration, p.p.m. | Sample Injected, microliters | Product Ratio | Comment |
|---|---|---|---|---|---|
| 1 | 350 | 0.1 | 20 | 0.42 | No Degradation |
| 2 | 350 | 0.1 | 40 | 0.73 | " |

Table 2-continued

| Ref. No. | Oven Temperature, °C. | Platinum Concentration, p.p.m. | Sample Injected, microliters | Product Ratio | Comment |
|---|---|---|---|---|---|
| 3 | 350 | 0.1 | 80 | 0.35 | " |
| 4 | 350 | 0.1 | 160 | 0.21 | " |
| 5 | 350 | 0.25 | 20 | 0.41 | " |
| 6 | 350 | 0.25 | 40 | 0.50 | " |
| 7 | 350 | 0.25 | 80 | 0.45 | " |
| 8 | 350 | 0.25 | 160 | 0.30 | " |
| 9 | 350 | 0.5 | 20 | 0.46 | Degradation |
| 10 | 300 | 1.0 | 20 | 0.33 | No Degradation |
| 11 | 350 | 1.0 | 20 | 0.48 | " |
| 12 | 400 | 1.0 | 20 | 0.42 | Degradation |
| 13* | 350 | 0.1 | 80 | 0.82 | " |
| 14* | 350 | 0.1 | 160 | 1.08 | " |

*In these experiments, no helium was used and the tube was 1.829 meters long.

EXAMPLE 4

A composition was prepared by thoroughly mixing 63 grams of a phenylmethylvinylsiloxy endblocked polydimethylsiloxane having a viscosity of 400 centistokes at 25°C., 33 grams of 5 micron quartz and 12 parts by weight platinum per one million parts by weight total composition wherein the platinum was added in the form described in Example 1. To this mixture was added and thoroughly mixed in 4.86 grams of trimethylsiloxy endblocked polyorganosiloxane having an average of five methylhydrogensiloxane units and three dimethylsiloxane units. The resulting mixture cured in one hour at room temperature to a coherent solid elastomer and at 150°C. in 2 minutes.

The above composition was prepared again except 0.00166 moles of the mono-adduct obtained in pure form in Example 2 was mixed with the hydrogen containing trimethylsiloxy endblocked polyorganosiloxane. This mixture cured at 150°C. in two minutes to an elastomer but did not cure in 10 days at room temperature.

That which is claimed is:

1. A method of reacting an acetylenic alcohol with a siloxane compond having at least three silicon-bonded hydrogen atoms bonded to at least three different silicon atoms in the presence of a platinum catalyst to provide an olefinic siloxane compound wherein the olefinic siloxane compound is an inhibitor for the platinum catalyst
   comprising passing a vaporized mixture of acetylenic alcohol, a soluble platinum catalyst and siloxane compound having at least three silicon-bonded hydrogen atoms through a tube heated at a temperature of from 210°C. to 450°C. and collecting a reaction product which is an olefinic siloxane compound which is, below 100°C., an inhibitor for the reaction between the acetylenic alcohol and the siloxane compound having at least three silicon-bonded-hydrogen atoms in the presence of a platinum catalyst, said mixture containing from 0.01 to 2 parts by weight platinum per one million parts by weight mixture.

2. The method in accordance with claim 1 in which the reaction product is distilled at reduced pressure to separate the olefinic siloxane compound from any unreacted starting reactants and any by-produced materials.

3. The method in accordance with claim 1 in which the reaction product vapors coming from the heated tube are passed through a series of condensers which are at temperatures decreasing from the condenser immediately connected to the heated tube such that the highest boiling compound is condensed and separated from the reaction product first and the lowest boiling compound of the reaction mixture is last to be condensed.

4. The method in accordance with claim 1 in which the mixture is passed through the heated tube with an inert carrier gas.

5. The method in accordance with claim 1 in which the residence time of the mixture in the heated tube is from 5 seconds to 120 seconds.

6. The method in accordance with claim 4 in which the residence time of the mixture in the heated tube is from 5 seconds to 120 seconds.

7. The method in accordance with claim 1 in which the tube is heated to a temperature of from 300°C. to 400°C.

8. The method in accordance with claim 6 in which the tube is heated to a temperature of from 300°C. to 400°C.

9. The method in accordance with claim 7 in which the acetylenic alcohol is 3-methyl-1-butyn-3-ol.

10. the method in accordance with claim 8 in which the acetylenic alcohol is 3-methyl-l-butyn-3-ol.

11. The method in accordance with claim 9 in which the siloxane compound having at least three silicon-bonded hydrogen atoms is a siloxane of the formula

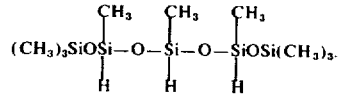

12. The method in accordance with claim 9 in which the siloxane compound having at least three silicon-bonded hydrogen atoms is a siloxane of the formula

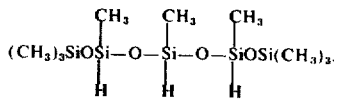

13. The method in accordance with claim 1 in which the platinum catalyst is present in amounts sufficient to provide from 0.01 to 1.0 parts by weight platinum per one million parts by weight of the mixture.

14. The method in accordance with claim 12 in which the platinum catalyst is present in amounts sufficient to provide from 0.01 to 1.0 parts by weight platinum per one million parts by weight of the mixture.

* * * * *

UNITED STATES PATENT AND TRADEMARK OFFICE
CERTIFICATE OF CORRECTION

PATENT NO. : 3,933,882
DATED : January 20, 1976
INVENTOR(S) : CHI-LONG LEE ET AL.

It is certified that error appears in the above-identified patent and that said Letters Patent are hereby corrected as shown below:

Column 9, line 41, "compond" should read --compound--.

Column 10, line 39, "the" should read --The--.

Column 10, line 50, "The method in accordance with claim 9" should read -- The method in accordance with claim 10 --.

Signed and Sealed this eleventh Day of May 1976

[SEAL]

Attest:

RUTH C. MASON
Attesting Officer

C. MARSHALL DANN
Commissioner of Patents and Trademarks